United States Patent [19]

Hoeksema et al.

[11] 4,107,295

[45] Aug. 15, 1978

[54] ANTIBIOTIC RUBRADIRIN B AND PROCESS FOR PREPARING THE SAME

[75] Inventors: Herman Hoeksema, Kalamazoo; Fritz Reusser, Portage; Donald R. Wait, Paw Paw, all of Mich.

[73] Assignee: The Upjohn Company, Kalamazoo, Mich.

[21] Appl. No.: 787,833

[22] Filed: Apr. 15, 1977

Related U.S. Application Data

[63] Continuation-in-part of Ser. No. 783,817, Apr. 1, 1977, abandoned.

[51] Int. Cl.² ............... A61K 35/00; G07F 11/00
[52] U.S. Cl. ............... 424/120; 195/80 R; 424/248.54; 544/99
[58] Field of Search ............... 424/120, 248.54; 544/99

[56] References Cited

U.S. PATENT DOCUMENTS 3,335,057   8/1967   Johnson et al. ............... 424/120

OTHER PUBLICATIONS

Bhuyan et al., Chem. Abst., vol. 63, 1965, pp. 3578h and 3579a.

*Primary Examiner*—Albert T. Meyers
*Assistant Examiner*—Daren M. Stephens
*Attorney, Agent, or Firm*—Roman Saliwanchik

[57] ABSTRACT

Antibiotic rubradirin B producible by the controlled fermentation of the known microorganism *Streptomyces achromogenes* var. *rubradiris*, NRRL 3061. This antibiotic and its base-addition salts are active against various microorganisms, for example, *Staphylococcus aureus*, *Streptococcus hemolyticus*, *Sarcina lutea*, and *Mycobacterium avium*. Accordingly, they can be used in various environments to eradicate or control such microorganisms.

7 Claims, 2 Drawing Figures

ANTIBIOTIC RUBRADIRIN B AND PROCESS FOR PREPARING THE SAME

CROSS REFERENCE TO RELATED APPLICATION

This application is a continuation-in-part of our pending application Ser. No. 783,817 filed on Apr. 1, 1977, now abandoned

BACKGROUND OF THE INVENTION

Antibiotic rubradirin and a microbiological process for its preparation, is disclosed in U.S. Pat. No. 3,335,057.

BRIEF SUMMARY OF THE INVENTION

The novel antibiotic of the invention, rubradirin B, is obtained by culturing *Streptomyces achromogenes* var. *rubradiris*, NRRL 3061, in an aqueous nutrient medium under aerobic conditions. The fermentation conditions disclosed in U.S. Pat. No. 3,335,057, referred to above, can be used to prepare rubradirin B.

DETAILED DESCRIPTION OF THE INVENTION

Chemical and Physical Properties of Rubradirin B

Molecular Weight: 795 (determined by field desorption mass spectroscopy).

Elemental Analysis: Calculated for $C_{40}H_{33}N_3O_{15}$: C, 60.38; H, 4.18; N, 5.28. Found: C, 59.25; H, 4.38; N, 5.17.

Melting Point: > 265° Dec.

Ultraviolet Absorption Spectrum

Figure 2:
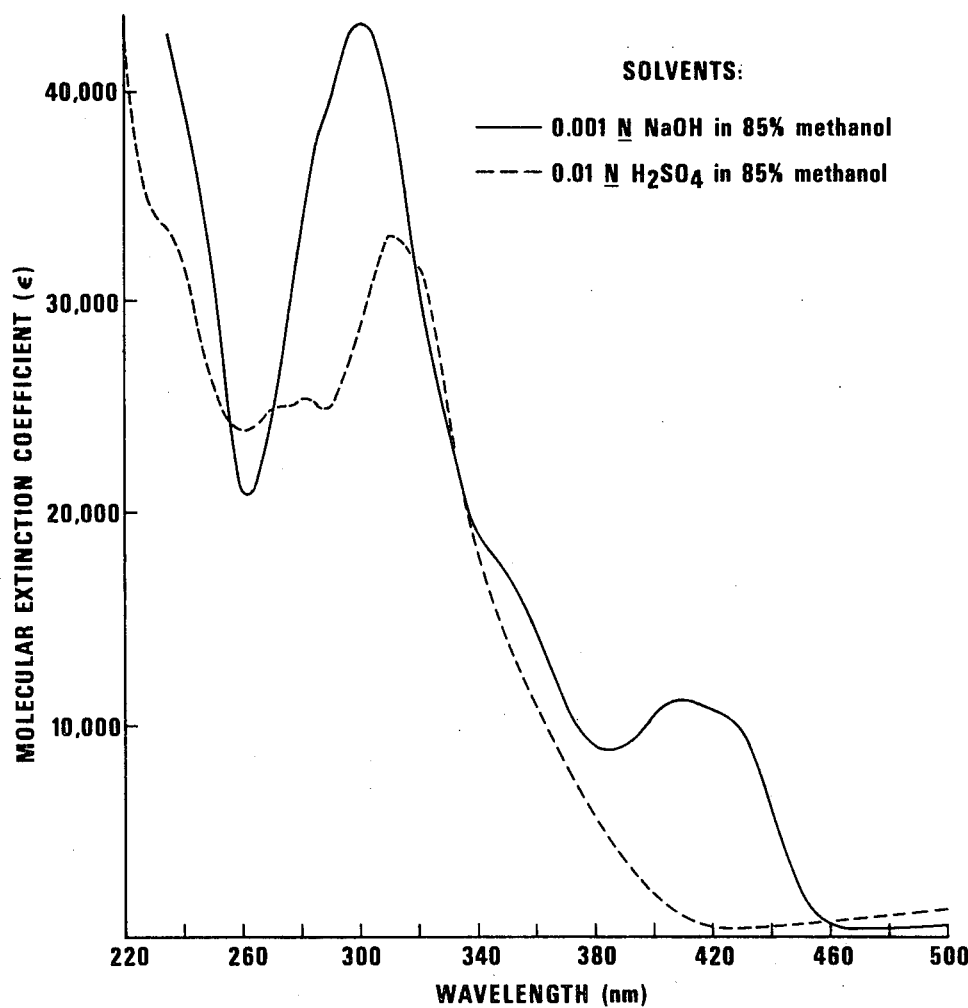

The ultraviolet absorption maxima of rubradirin B, as reproduced in FIG. 2 of the drawings are:

In 0.001 N methanolic NaOH, $\lambda$, ($\epsilon$): 248 sh (32,060), 303 (43,450), 345 sh (17,000), 408 (11,200), 422 sh (10,550). In 0.01 N methanolic $H_2SO_4$, $\lambda$, ($\epsilon$): 240 sh (33,000), 278 sh (25,000), 283 (25,100), 315 (33,000), 323 sh (32,500).

Infrared Absorption Spectra

Figure 1:
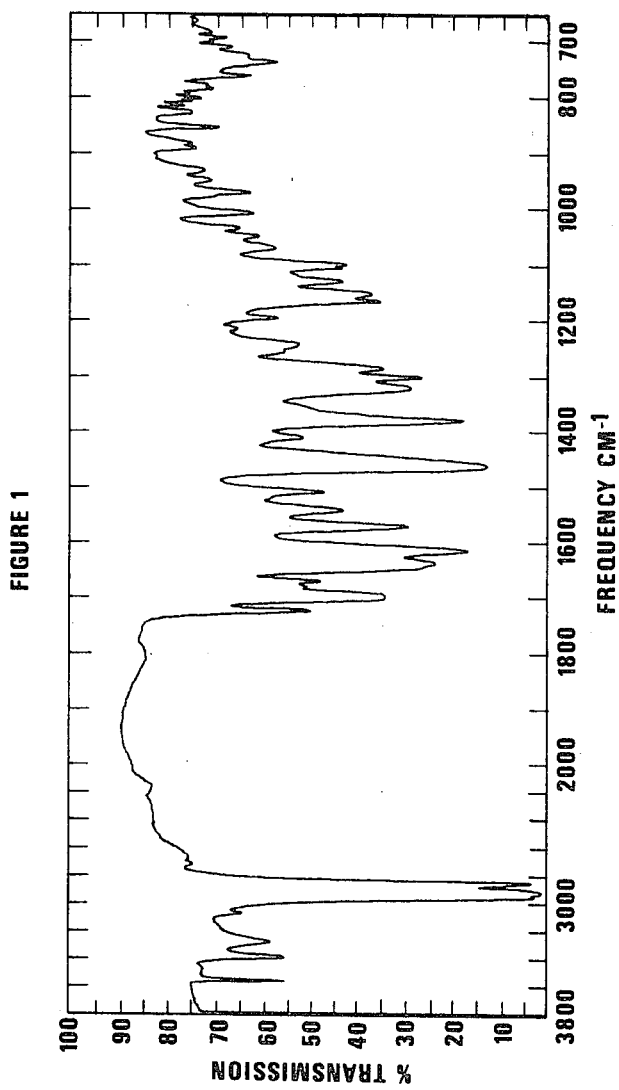

Rubradirin B has a characteristic infrared absorption spectrum in a mineral oil mull as shown in FIG. 1 of the drawings. Peaks are observed at the following wave lengths expressed in reciprocal centimeters:

| Band Frequency (Wave Numbers) | Intensity |
| --- | --- |
| 3560 | M |
| 3390 | M |
| 3280 | M |
| 3080 | W |
| 2950 | S |
| 2920 | S |
| 2850 | S |
| 2720 | W |
| 2670 | W |
| 2170 | W |
| 1723 | M |
| 1697 | M |
| 1680 | M |
| 1667 | M |
| 1635 | S |
| 1612 | S |
| 1570 | S |
| 1540 | M |
| 1508 | M |
| 1462 | S |
| 1410 | M |
| 1377 | S |
| 1357 | S, sh (sh=shoulder) |
| 1320 | S |
| 1300 | S |
| 1283 | M |
| 1255 | M |
| 1240 | M |
| 1215 | W |
| 1192 | M |
| 1162 | M |
| 1150 | M |
| 1127 | M |
| 1102 | M |
| 1098 | M |
| 1068 | M |
| 1045 | W |
| 1032 | W |
| 1005 | W |
| 967 | W |
| 948 | W |
| 928 | W |
| 890 | W |
| 880 | W |
| 853 | W |
| 825 | W |
| 812 | W |
| 805 | W |
| 800 | W |
| 782 | W |
| 776 | W |
| 760 | W |
| 735 | M |
| 723 | W |
| 708 | W |
| 698 | W |
| 695 | W |
| 680 | W |

Key: S=Strong M=Medium and W=Weak

Rubradirin B also has a characteristic infrared absorption spectrum when pressed in a KBr disc. Peaks are observed at the following wavelengths expressed in reciprocal centimeters:

| Band Frequency (Wave Numbers) | Intensity |
| --- | --- |
| 3560 | M |
| 3380 | M |
| 3280 | M |
| 3080 | W |
| 2970 | W |
| 2930 | W |
| 2850 | W |
| 2170 | W |
| 1724 | M |
| 1698 | S |
| 1668 | M |
| 1638 | S |
| 1615 | S |
| 1570 | S |
| 1540 | M |
| 1508 | M |
| 1460 | S |
| 1410 | M |
| 1382 | S |
| 1323 | S |
| 1298 | S |
| 1281 | S |
| 1240 | M |
| 1195 | M |
| 1163 | S |
| 1125 | M |
| 1102 | M |
| 1094 | M |
| 1065 | M |
| 1048 | M |
| 1030 | M |
| 1005 | M |
| 968 | M |
| 947 | W |
| 927 | W |
| 890 | W |
| 877 | W |
| 852 | W |
| 825 | W |
| 810 | W |
| 805 | W |
| 800 | W |
| 792 | W |
| 781 | W |
| 758 | M |

-continued

| Band Frequency (Wave Numbers) | Intensity |
| --- | --- |
| 732 | M |
| 708 | M |
| 690 | M |
| 680 | M |

Solubilities

The novel compound of the invention is soluble in aqueous bases above pH 7.5 and insoluble in water below pH 6.0. It is also soluble in lower alkyl amides such as dimethylformamide and dimethylacetamide, and in dimethylsulfoxide and ethyl acetate which is saturated with water. It is very slightly soluble in lower alcohols (methanol and ethanol), chloroform, and tetrahydrofuran. It is insoluble in hydrocarbon solvents such as benzene, toluene, and the alkanes (pentane through the higher alkanes).

Antibacterial Spectrum of Rubradirin B

Rubradirin B shows the following zones of inhibition in millimeters (mm) on a standard disc plate assay (12.7 mm assay discs) at a concentration of 0.5 mg/ml.

| Microorganism | Zone of Inhibition |
| --- | --- |
| Staphylococcus aureus | 26 |
| Sarcina lutea | 29 |
| Mycobacterium avium | 25 |
| Bacillus subtilis | 0 |

On testing rubradirin B by a microplate broth dilution assay using the medium BHI (Brain Heart Infusion), the following spectrum was observed.)

| Microorganism | Minimum Inhibitory Concentration (mcg/ml) |
| --- | --- |
| Staphylococcus aureus 284 UC 76 ® | 1.5 |
| Staphylococcus aureus UC 570 ® | 3.1 |
| Staphylococcus aureus UC 746 ® | .78 |
| Streptococcus hemolyticus UC 152 ® | 6.2 |
| Streptococcus faecalis UC 694 ® | > 100 |
| Escherichia coli UC 45 ® | > 100 |
| Proteus vulgaris UC 93 ® | > 100 |
| Klebsiella pneumoniae UC 58 ® | > 100 |
| Salmonella schottmuelleri UC 126 ® | > 100 |
| Pseudomonas aeruginosa UC 95 ® | > 100 |
| Diplococcus pneumoniae UC 41 ® | .39 |

"UC ®" is a registered trademark of the Upjohn Company Culture Collection. These cultures can be obtained from The Upjohn Company in Kalamazoo, Mich., upon request.

Rubradirin B was tested in vivo in mice. Mice infected with S. aureus were protected subcutaneously with a $CD_{50}$ of 98 mg/kg.

THE MICROORGANISM

The microorganism used for the production of rubradirin B is the known microorganism Streptomyces achromogenes var. rubradiris, NRRL 3061. This culture is available to the public upon request to the culture repository at Peoria, Ill. The characteristics of this culture are disclosed in U.S. Pat. No. 3,335,057. Columns 2–4.

The new compound of the invention is produced when the elaborating organism is grown in an aqueous nutrient medium under submerged aerobic conditions. It is to be understood also that for the preparation of limited amounts surface cultures in bottles can be employed. The organism is grown in a nutrient medium containing a carbon source, for example, an assimilable carbohydrate, and a nitrogen source, for example, an assimilable nitrogen compound or proteinaceous material. Preferred carbon sources include glucose, brown sugar, sucrose, glycerol, starch, corn starch, lactose, dextrin, molasses, and the like. Preferred nitrogen sources include corn steep liquor, yeast, autolyzed brewer's yeast with milk solids, soybean meal, cottonseed meal, corn meal, milk solids, pancreatic digest of casein, distillers' solubles, animal peptone liquors, meat and bone scraps, and the like. Combination of these carbon and nitrogen sources can be used advantageously. Trace metals, for example, zinc, magnesium, manganese, cobalt, iron, and the like need not be added to the fermentation media since tap water and unpurified ingredients are used as media components. Production of the compound of the invention can be effected at any temperature conducive to satisfactory growth of the microorganism, for example, between about 18° and 40° C. and preferably between about 26° and 30° C. Ordinarily, optimum production of the compound is obtained in about 2 to 10 days. The medium normally stays fairly close to neutral, or on the alkaline side during the fermentation. The final pH is dependent, in part, on the buffers present, if any, and in part on the initial pH of the culture medium which is advantageously adjusted to about pH 6–8 prior to sterilization.

When growth is carried out in large vessels and tanks, it is preferable to use the vegetative form, rather than the spore form, of the microorganism for inoculation to avoid a pronounced lag in the production of the new compound and the attendant inefficient utilization of the equipment. Accordingly, it is desirable to produce a vegetative inoculum in a nutrient broth culture by inoculating the broth culture with an aliquot from a soil or slant culture. When a young, active, vegetative inoculum has thus been secured, it is transferred aseptically to large vessels or tanks. The medium in which the vegetative inoculum is produced can be the same as, or different from, that utilized for the production of the new compound, as long as it is such that a good growth of the microorganism is obtained.

A variety of procedures can be employed in the isolation and purification of rubradirin B, for example, solvent extraction, liquid-liquid distribution in a Craig apparatus, the use of adsorbents, precipitation from beer at acid pH, and crystallization from solvents. Acid precipitation procedures are preferred for recovery inasmuch as they are less time consuming and less expensive, and higher recovery yields are obtained thereby.

In a preferred process, rubradirin B is recovered from its culture medium by separation of the mycelia and undissolved solids by conventional means such as by filtration or centrifugation. The antibiotic is then removed from the filtered beer by adjusting the pH to about 4.0 with sulfuric acid. The precipitate which forms is removed by filtration, using a filter aid such as Dicalite. The cake is then eluted with acetone or ethyl acetate. The cake eluates are concentrated to an aqueous mixture and freeze-dried. The dried material is leached with acetone or ethyl acetate and the solvent phase is concentrated, then diluted with four volumes of Skellysolve B (isomeric hexanes). The rubradirin complex is filtered off and dried.

Crude preparations of rubradirin B can be subjected to silica gel chromatography to obtain essentially pure rubradirin B. A suitable solvent system in this procedure can be chloroform:methanol (97:3). Alternatively, essentially pure rubradirin B can be obtained by subjecting a crude preparation of rubradirin B to chromatography on a partition column consisting of diatomaceous earth buffered at pH 10 with an aqueous solution of 0.2 M sodium carbonatebicarbonate. The column can be developed with a solvent system consisting of ethyl acetate:1-butanol, buffer (2:2:1).

Salts of rubradirin B are formed employing the free acid of rubradirin B and an inorganic or organic base. The rubradirin B salts can be prepared as for example by suspending rubradirin B free acid in water, adding a dilute base until the pH of the mixture is about 7 to 8, and freeze-drying the mixture to provide a dried residue consisting of the rubradirin B salt. Rubradirin B salts which can be formed include the sodium, potassium, and calcium. Other salts of rubradirin B including those with organic bases such as primary, secondary, and tertiary mono-, di-, and poly-amines can also be formed using the above-described or other commonly employed procedures.

The new compound of the invention, rubradirin B, inhibits the growth of the following organisms: *Staphylococcus aureus, Diplococcus pneumoniae, Sarcina lutea, Mycobacterium avium,* and *Streptococcus hemolyticus.* Accordingly, the new compound can be used as a disinfectant on various dental and medical equipment contaminated with *Staphlococcus aureus;* it can also be used as a disinfectant on washed and stacked food utensils contaminated with this organism. Rubradirin B also can be used to control *Mycobacterium avium* which is a known producer of generalized tuberculosis in birds and rabbits.

The following examples are illustrative of the process and products of the present invention, but are not to be construed as limiting. All percentages are by weight, and solvent mixture proportions are by volume unless otherwise noted.

EXAMPLE 1

A. Fermentation

An agar slant of *Streptomyces achromogenes* var. *rubradiris,* NRRL 3061, is used to inoculate a series of 500-ml Erlenmeyer flasks each containing 100 ml of sterile seed medium consisting of the following ingredients:

| | |
|---|---|
| Glucose monohydrate | 25 g/liter |
| Pharmamedia* | 40 g/liter |
| Tap water q.s. | 1 liter |

*Pharmamedia is an industrial grade of cottonseed flour produced by Traders Oil Mill Company, Fort Worth, Texas.

The flasks are incubated for 3 days at 28° C. on a Gump rotary shaker operating at 250 r.p.m.

Seed inoculum (5%), prepared as described above, is used to inoculate a series of 500-ml Erlenmeyer flasks each containing 100 ml of sterile fermentation medium consisting of the following ingredients:

| | |
|---|---|
| Starch | 10 g/liter |
| Corn steep liquor | 20 g/liter |
| Distiller' solubles | 15 g/liter |
| Mg (NO$_3$)$_2$ .6H$_2$O | 3.8 g/liter |

| | |
|---|---|
| -continued | |
| Tap water q.s. | 1 liter |

The fermentation medium presterilization pH is 7.2.

The fermentation flasks are incubated at 28° C. on a Gump rotary shaker operating at 250 r.p.m. The fermentation flasks are harvested after about 3 to 4 days. A typical shake flask fermentation is depicted below. The assay is against the microorganism *Sarcina lutea.* It is a disc plate assay using 0.1 M phosphate buffer, pH 7.85, as diluent.

| Day | Assay, Biounit/ml |
|---|---|
| 1 | trace |
| 2 | 104 |
| 3 | 160 |
| 4 | 64 |

NOTE: One Biounit corresponds to the dilution factor of the sample to yield an inhibition zone of 20 mm.

B. Recovery

Whole broth from a fermentation, as described above, is slurried with 4 percent of its weight of diatomaceous earth and filtered. The filter cake is washed with 1/10 volume of water and the wash is added to the clear beer. The clear beer is adjusted to pH 4.0 with 6 N sulfuric acid and filtered with the aid of Dicalite. The spent beer is discarded. The wet cake is leached with ethyl acetate and the solvent phase is then concentrated to an aqueous phase. The latter is freeze-dried. The residue is dissolved in ethyl acetate and diluted with 4 volumes of Skellysolve B. The precipitate which is collected and dried contains a mixture including rubradirin and rubradirin B.

C. Purification

A one gram quantity of crude preparation containing rubradirin B, prepared as described above, is chromatographed on 500 g of silica gel G (70–230 mesh, E. Merck), buffered at pH 5.8. The first elution with 1500 ml of chloroform is discarded. Thereafter 20 ml fractions are collected. Tubes 201 to 470 contain rubradirin by tlc (thin layer chromatography). The elution solvent is changed to chloroform:methanol (97:3). Tubes 471-510 contain a mixture of rubradirin and rubradirin B. The solids in this fraction are isolated by concentration and precipitation in Skellysolve B, 310 mg.

The combined solids from the above chromatography and 2 similar ones, 660 mg total, are then dissolved and suspended in 30 ml of chloroform, and this is stirred for 1 hour and filtered. The semicrystalline precipitate, 160 mg, is found to be essentially pure rubradirin B by tlc.

The tlc is run on Eastman silica gel (#6060) sheets with the solvent system ethyl acetate-acetone-water (8:5:1) and bioautographed on trays seeded with *S. lutea.* Approximately 0.5 γ of line product preparations and correspondingly lesser amounts of higher purity preparations are applied for analyses.

Preparations are assayed after they have been adjusted to pH 3.0 and dried in vacuum. Dilutions are made in methanol and a quantity of .08 ml is applied to 12.7 mm assay discs which are dried and placed on agar trays seeded with *S. lutea.* Assays are expressed as biounits.

EXAMPLE 2

Sodium Salt Of Rubradirin B

Twenty-five mg of rubradirin B as prepared in Example 1 is dissolved in several drops of acetone. To this solution is added 0.5 ml of water and 1 drop of 6 N sodium hydroxide, followed by the addition of sufficient ether to precipitate the sodium salt of rubradirin B.

The tentative structure of rubradirin B can be shown as follows:

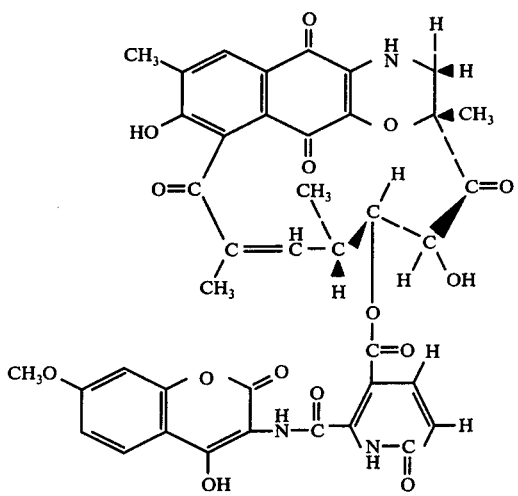

We claim:

1. Essentially pure rubradirin B, a compound which
   (a) is effective in inhibiting the growth of various bacteria;
   (b) is soluble in dimethylformamide, dimethylsulfoxide and aqueous base, and is insoluble in aqueous acid and hydrocarbon solvents;
   (c) has the following elemental analysis: C, 59.25; H, 4.38; N, 5.17;
   (d) has a molecular weight of 795 (determined by field desorption mass spectroscopy);
   (e) has a characteristic infrared absorption spectrum as shown in FIG. 1 of the accompanying drawings;
   (f) has a characteristic ultraviolet absorption spectrum as shown in FIG. 2 of the accompanying drawings;
   (g) has a melting point > 265° Dec.; and,
   (h) has a molecular formula $C_{40}H_{33}N_3O_{15}$.

2. A compound selected from the group consisting of rubradirin B, according to claim 1, and salts thereof with alkali metal, alkaline earth metals, and amines.

3. Sodium salt of rubradirin B, said rubradirin B defined in claim 1.

4. A process for recovering rubradirin B from a fermentation using *Streptomyces achromogenes* var. *rubradiris*, NRRL 3061, which comprises:
   (a) filtering said fermentation beer to obtain a filtrate containing rubradirin B;
   (b) adjusting the pH of the filtrate to about 4.0 to form a precipitate containing rubradirin B;
   (c) removing said precipitate by filtration and eluting the filter cake which forms with a solvent for rubradirin B to give eluates containing rubradirin B;
   (d) concentrating said eluates to a residue;
   (e) leaching said residue with a solvent for rubradirin B and concentrating the solvent;
   (f) diluting said solvent concentrate with a solvent in which rubradirin B is not soluble to form a precipitate containing rubradirin B;
   (g) isolating and drying said precipitate containing rubradirin B to a solid; and,
   (h) subjecting said solid containing rubradirin B to silica gel chromatography and isolating essentially pure rubradirin B.

5. A process, according to claim 4, wherein the solvent for rubradirin B is ethyl acetate.

6. A process, according to claim 4, wherein the solvent in which rubradirin B is not soluble in is isomeric hexanes.

7. A process, according to claim 4, wherein rubradirin B is isolated in the essentially pure form from the silica gel chromatography by elution of said silica gel first with chloroform, then with the solvent system chloroform: methanol (97:3).

* * * * *